(12) United States Patent
Lee et al.

(10) Patent No.: US 9,170,141 B2
(45) Date of Patent: Oct. 27, 2015

(54) DEVICE FOR MEASURING DROPLET MASS FLUX DISTRIBUTIONS TO TEST SPRAY INJECTION SYSTEM AND THE MEASURING METHOD

(75) Inventors: In Chul Lee, Seoul (KR); Do Hun Kim, Seoul (KR); Ja Ye Koo, Goyang-si (KR)

(73) Assignee: UNIVERSITY INDUSTRY COOPERATION FOUNDATION KOREA AEROSPACE UNIVERSITY, Goyang-Si, Gyeonggi-Do (KR)

( * ) Notice: Subject to any disclaimer, the term of this patent is extended or adjusted under 35 U.S.C. 154(b) by 344 days.

(21) Appl. No.: 13/878,541

(22) PCT Filed: Oct. 27, 2011

(86) PCT No.: PCT/KR2011/008078
§ 371 (c)(1),
(2), (4) Date: Apr. 9, 2013

(87) PCT Pub. No.: WO2012/057542
PCT Pub. Date: May 3, 2012

(65) Prior Publication Data
US 2013/0192385 A1  Aug. 1, 2013

(30) Foreign Application Priority Data
Oct. 29, 2010  (KR) ........................ 10-2010-0106652

(51) Int. Cl.
*G01F 1/76*  (2006.01)
*G01M 99/00*  (2011.01)
(Continued)

(52) U.S. Cl.
CPC ............... *G01F 1/76* (2013.01); *G01M 99/008* (2013.01); *A61M 5/1689* (2013.01); *A61M 5/16895* (2013.01); *G01F 1/007* (2013.01); *G01F 1/704* (2013.01); *G01F 13/00* (2013.01)

(58) Field of Classification Search
CPC ........... G01F 1/76; G01F 13/00; G01F 1/704; G01F 1/007; A61M 5/16895; A61M 5/1689; A61M 2205/3317
USPC ....................................................... 73/861.41
See application file for complete search history.

(56) References Cited

U.S. PATENT DOCUMENTS 3,459,049 A * 8/1969 Kamps ........................ 73/865.9
5,686,989 A * 11/1997 Hoffman et al. .............. 356/336
(Continued)

FOREIGN PATENT DOCUMENTS

JP           11-352021 A     12/1999
KR     1020020014572 A      2/2002
(Continued)

OTHER PUBLICATIONS

"Spray Patternation at High pressure", Cohen et al., Jul. 10-12, 1989, Paper 89/2323 at AIAA/ASME/SAE/ASEE 25th Joint Propulsion Conference.*
(Continued)

*Primary Examiner* — Lisa Caputo
*Assistant Examiner* — Tran M Tran
(74) *Attorney, Agent, or Firm* — Novick, Kim & Lee, PLLC; Jae Youn Kim (57) ABSTRACT

A technology to measure the mass flux distribution of liquid spray to evaluate droplet dispersion of a spray device for liquids such as fuel, paints, or coating agents, is provided. The apparatus for measuring spray mass flux to evaluate the droplet dispersion of the spray device includes a liquid spraying part including a spray nozzle to spray liquid, a spray collecting part to collect the liquid sprayed from the liquid spraying part, a transfer tube to transfer the liquid collected in the spray collecting part, a multi-cylinder part including a plurality of cylinders to receive the liquid collected in the spray collecting part, a movable mass measurement part to measure a mass of each cylinder of the multi-cylinder part, and a mass flux calculating part to calculate a distribution graph of mass flux of the sprayed liquid.

9 Claims, 7 Drawing Sheets

(51) Int. Cl.
*G01F 1/00* (2006.01)
*G01F 1/704* (2006.01)
*G01F 13/00* (2006.01)
*A61M 5/168* (2006.01)

(56) References Cited

U.S. PATENT DOCUMENTS

| | | | | |
|---|---|---|---|---|
| 6,298,719 | B1 * | 10/2001 | Schoeffel et al. | 73/114.46 |
| 6,508,112 | B1 * | 1/2003 | Verhoeven | 73/114.46 |
| 7,469,570 | B2 * | 12/2008 | Cooper | 73/1.73 |
| 8,002,379 | B2 * | 8/2011 | Kamiyama | 347/19 |
| 2007/0242871 | A1 * | 10/2007 | Prociw et al. | 382/141 |

FOREIGN PATENT DOCUMENTS

| | | | |
|---|---|---|---|
| KR | 1020040009474 | A | 1/2004 |
| KR | 1020040051297 | A | 6/2004 |
| KR | 20050056627 | * | 6/2005 |
| KR | 1020050056627 | A | 6/2005 |

OTHER PUBLICATIONS

Mechanical Patternator, image from Wikipedia page, accessed Apr. 23, 2015.*

* cited by examiner

DEVICE FOR MEASURING DROPLET MASS FLUX DISTRIBUTIONS TO TEST SPRAY INJECTION SYSTEM AND THE MEASURING METHOD

TECHNICAL FIELD

The present invention relates to a technology to measure the mass flux distribution of liquid spray to evaluate droplet dispersion of a spray device for liquids such as fuel, paints, or coating agents. In more particular, the present invention relates to an apparatus and a method for automatically calculating spray mass flux according to the total mass of the sprayed liquid by automatically measuring the mass of the sprayed liquid at each point of the sprayed liquid.

BACKGROUND ART

In general, to evaluate the performance of a product or an assembly employing liquid fuel, paints, or coating agents, an amount of sprayed liquid must be measured in relation to the sprayed area of the liquid. To this end, conventionally, a patternator (collector of sprayed droplets) has been mainly used.

The conventional patternator divides and measures a distribution amount of fluid sprayed in a liquid state according to sections. As liquid is sprayed, the liquid is sprayed to a region other than a tube provided in the collector, so that flux loss occurs, and an amount of liquid collected in a predetermined tube overflows to move to another tube, so that an amount of sprayed liquid cannot be exactly measured.

In addition, the mass of the liquid is manually measured by using a fountainpen filler or a scale to measure an amount of liquid collected in each tube, so that too much time is spent in the measurement work, and the accuracy of the measured value may be degraded.

DISCLOSURE

Technical Problem

Accordingly, the present invention has been made keeping in mind the above problems occurring in the prior art, and an object of the present invention is to provide an apparatus for measuring the spray mass flux to evaluate the droplet dispersion of a spray device, capable of calculating spray mass flux distribution according to liquid spraying regions by automatically measuring the masses of a plurality of cylinders receiving sprayed liquid.

Another object of the present invention is to prevent liquid, which is not introduced into a plurality of lattice cells or a plurality of tubes, from flowing out by providing a flux loss preventing plate.

Still another object of the present invention is to prevent liquid from being unstably collected in a liquid spraying initial stage by additionally providing a spray blocking layer.

Still another object of the present invention is to regularly arrange a plurality of cylinders constituting a multi-cylinder part and fix the arranged cylinders.

Still another object of the present invention is to provide a movable mass measurement part and move a load cell part of the movable mass measurement part left, right, forward, or backward to measure the mass of each cylinder.

Still another object of the present invention is to calculate the ratio of the total mass of the sprayed liquid to the mass of each cylinder and calculate 3-D mass flux distribution.

Still another object of the present invention is to calculate the total mass of the sprayed liquid by providing a flux measuring unit.

Still another object of the present invention is to provide a method for measuring the spray mass flux to evaluate the droplet dispersion of a spray device, capable of automatically calculating 3-D mass flux distribution according to masses of cylinders after collecting sprayed fuel and transferring the sprayed fuel into a multi-cylinder.

Still another object is to determine if the spraying operation state of a liquid spraying part is a normal state before liquid is sprayed.

Still another object is to open a spray blocking layer if the spraying operation state of the liquid spraying part is determined as the normal state.

Still another object is to exactly measure the mass of each cylinder by additionally initializing a movable mass measurement part.

Technical Solution

According to one aspect of the present invention, there is provided an apparatus for measuring spray mass flux to evaluate droplet dispersion of a spray device which includes a liquid spraying part including a spray nozzle to spray liquid, a spray collecting part provided below the liquid spraying part to collect the liquid sprayed from the liquid spraying part, a transfer tube linked with the spray collecting part to transfer the liquid collected in the spray collecting part, a multi-cylinder part including a plurality of cylinders accommodating one end of the transfer tube therein to receive the liquid collected in the spray collecting part, a movable mass measurement part placed below the multi-cylinder to measure a mass of each cylinder of the multi-cylinder part, and a mass flux calculating part linked with the spray collecting part and the movable mass measurement part to calculate a distribution graph of mass flux of the sprayed liquid.

According to the present invention, in the apparatus for measuring spray mass flux to evaluate the droplet dispersion of the spray device, the spray collecting part includes a plurality of lattice cells or a plurality of tubes, and is provided at a lower portion thereof with a flux loss preventing plate to prevent liquid, which is not introduced into the lattice cells or the tubes, from flowing out.

According to the present invention, the apparatus for measuring spray mass flux to evaluate the droplet dispersion of the spray device further includes a spray blocking layer provided at an upper portion of the spray collecting part to block the sprayed liquid.

According to the present invention, in the apparatus for measuring spray mass flux to evaluate the droplet dispersion of the spray device, the movable mass measurement part includes a load cell part to measure the mass of each cylinder, and a servo transfer module connected to a lower portion of the load cell part to transfer the load cell part in a row direction or a column direction so that the load cell part moves to a lower point of the cylinder to be measured.

According to another aspect of the present invention, there is provided a method for measuring spray mass flux to evaluate droplet dispersion of a spray device which includes spraying liquid by using a liquid spraying part, collecting the sprayed liquid by using a spray collecting part, measuring a flux of the liquid sprayed in the spray collecting part, moving the liquid, which is collected in the spray collecting part, to a multi-cylinder part by using a transfer tube, measuring masses of cylinders of the multi-cylinder part by using a movable mass measurement part, and calculating a 3-D mass flux distribution graph of the sprayed liquid by using a mass flux calculating part.

BEST MODE

[Mode for Invention]

Hereinafter, an apparatus and a method for measuring the spray mass flux to evaluate the droplet dispersion of a spray device according to the invention will be described in detail.

Figure 1:
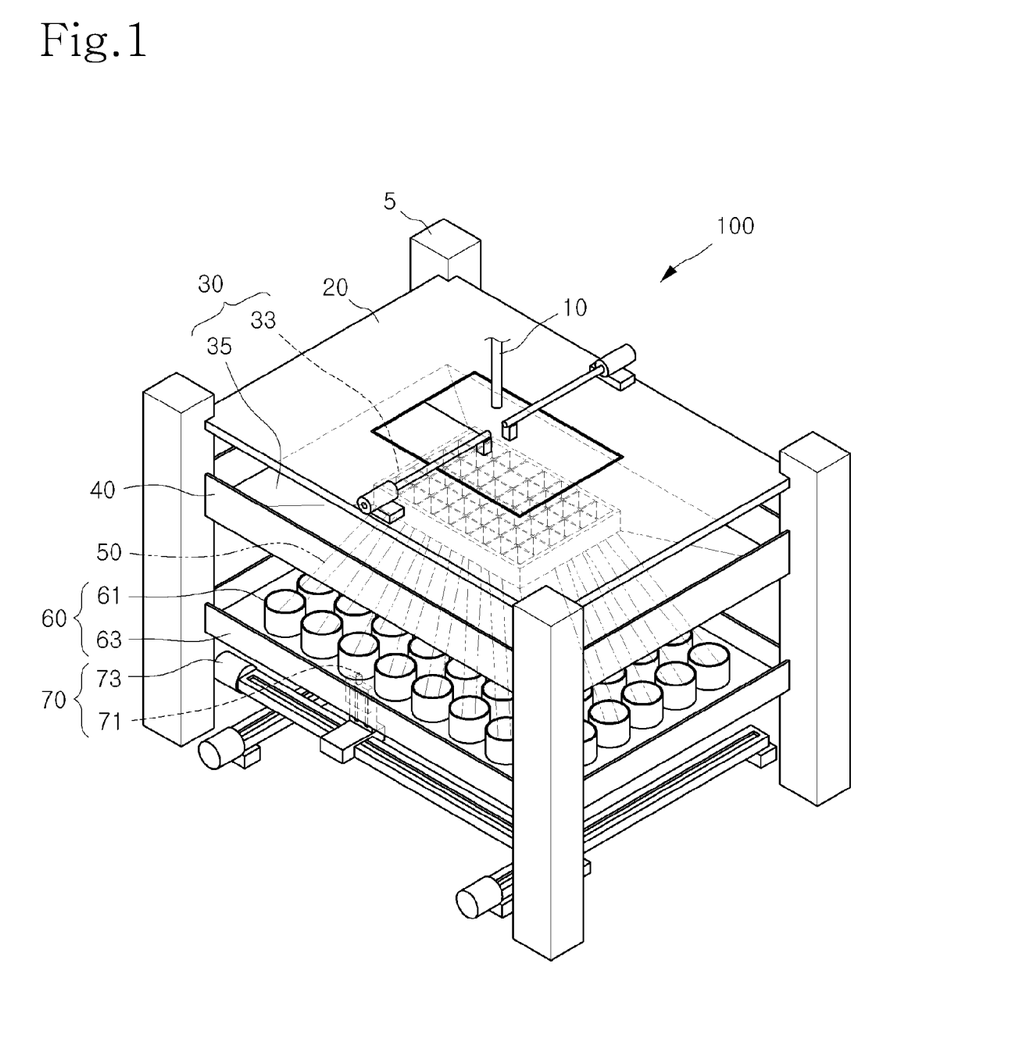
FIG. 1 is a perspective view showing an apparatus for measuring the spray mass flux to evaluate the droplet dispersion of a spray device according to one embodiment of the present invention.

FIG. 1 is a view showing an apparatus for measuring the spray mass flux to evaluate the droplet dispersion of a spray device according to one embodiment of the present invention. The apparatus for measuring the spray mass flux to evaluate the droplet dispersion of the spray device according to one embodiment of the present invention includes support frames 5, a liquid spraying part 10, a spray blocking layer 20, a spray collecting part 30, a lost flux measuring part 40, a transfer tube 50, a multi-cylinder part 60, a movable mass measurement part 70 and a mass flux calculating part (not shown in drawings).

The support frames 5 include fixing units to fix the liquid spraying part 10, the spray blocking layer 20, the spray collecting part 30, the lost flux measuring part 40, the transfer tube 50, and the multi-cylinder part 60, so that the liquid spraying part 10, the spray blocking layer 20, the spray collecting part 30, the lost flux measuring part 40, the transfer tube 50, and the multi-cylinder part 60 are stacked on each other while being spaced apart from each other. According to one embodiment of the present invention, the support frames 5 have the shape of a rectangular column to fix the corner of each component.

The liquid spraying part 10 includes a spray nozzle to spray liquid, and is provided above the center between the support frames 5.

The liquid according to the present invention includes fuels, paints, and coating agents.

In addition, preferably, the liquid spraying part 10 according to the present invention further include a flux measuring unit to measure the total mass of the sprayed liquid.

The spray collecting part 30 is provided below the liquid spraying part 10 to collect the liquid sprayed from the liquid spraying part 10. The spray collecting part 30 according to the present invention includes a plurality of lattice cells 33 or a plurality of tubes. The spray collecting part 30 includes a flux loss preventing plate 35 to prevent the liquid, which is not introduced into the lattice cells 33, from flowing out.

In addition, preferably, the apparatus for measuring the spray mass flux to evaluate the droplet dispersion of the spray device according to one embodiment of the present invention further includes a spray blocking layer 20 provided above the spray collecting part 30 so that the sprayed liquid can be blocked.

Figure 2:
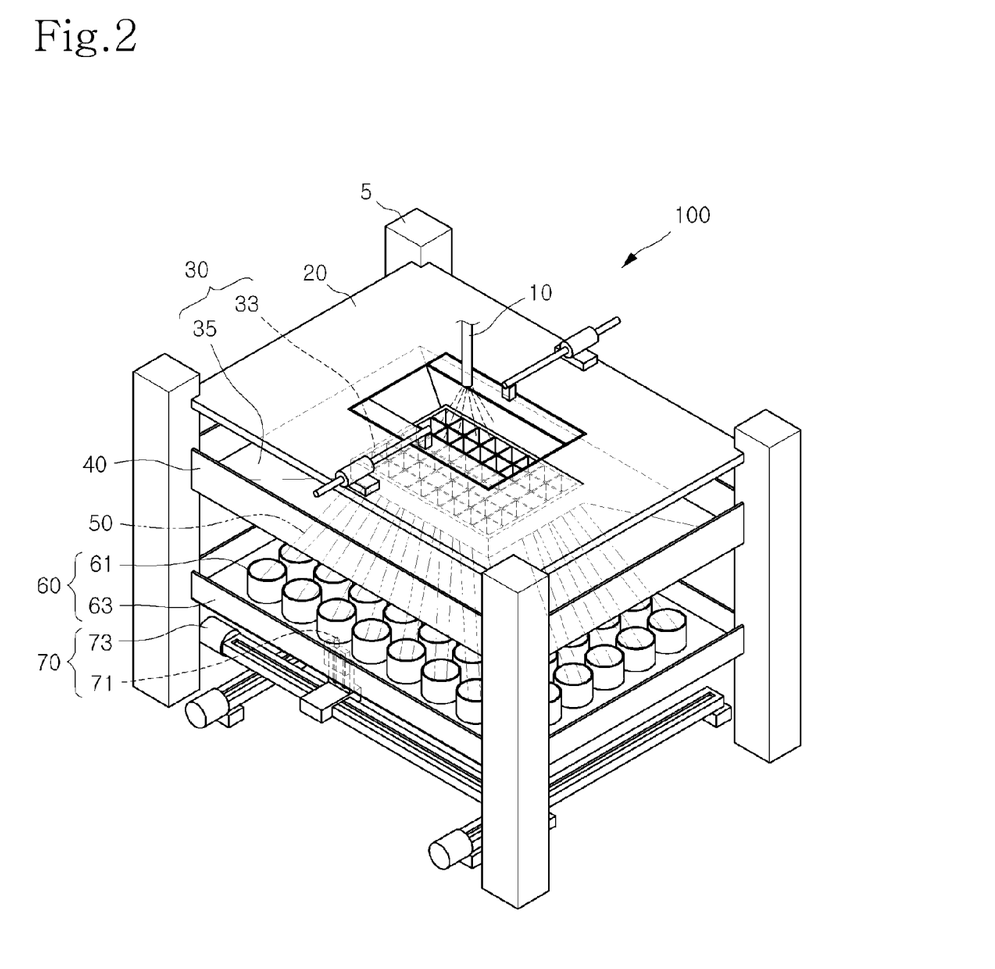
FIG. 2 is a view showing the operation of a spray blocking layer in the apparatus for measuring the spray mass flux to evaluate the droplet dispersion of the spray device according to the present invention.

As shown in FIG. 2, the spray blocking layer 20 blocks the sprayed liquid from being introduced into the spray collecting part 30 when the liquid spraying part 10 imperfectly performs a spray function. When the liquid spraying part 10 normally performs the spray function, the spray blocking layer 20 is open.

One end of the transfer tube 50 is connected to a lower portion of the spray collecting part 30, so that the liquid collected in the spray collecting part 30 can be transferred to the multi-cylinder part 60.

According to the embodiment of the present invention, the transfer tube 50 includes Teflon.

The multi-cylinder part 60 includes a plurality of cylinders accommodating the other end of the transfer tube 50 to receive the liquid collected in the spray collecting part 30.

In the multi-cylinder part 60, the cylinders 61 are arranged in the form of a matrix while being spaced apart from each other by a predetermined distance. Preferably, the multi-cylinder part 60 includes cylinder holders 63 to fix the outer portions of the cylinders 61.

The movable mass measurement part 70 is positioned below the multi-cylinder part 60 to measure the weight of each cylinder 61.

Figure 3:
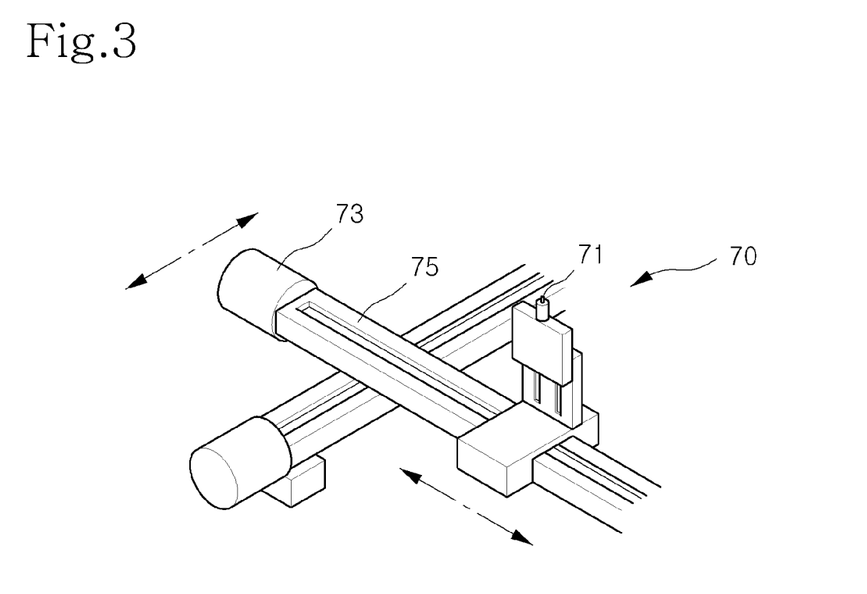
FIG. 3 is a view showing the detailed structure of a movable mass measurement part in the apparatus for measuring the spray mass flux to evaluate the droplet dispersion of the spray device according to the present invention.

As shown in FIG. 3, preferably, the movable mass measurement part 70 according to the present invention includes a load cell part 71 to measure the mass of each cylinder 61 and servo transfer modules 73 connected to the lower portion of the load cell part 71 to move the load cell part 71 in a row direction or a column direction so that the load cell part 71 can move to a lower point of the cylinder 61 for mass measurement.

According to the embodiment of the present invention, the servo transfer modules 73 include movable wheels and transfer rails 75 to move the load cell part 71 forward, reward, left or right.

A mass flux calculating part is linked to the spray collecting part 30 and the movable mass measurement part 70 to calculate the distribution graph of the mass flux of the sprayed liquid. According to the present invention, the mass flux calculating part calculates 3-D mass flux distribution according to the coordinates of a sprayed liquid region by using a liquid mass ratio of the total mass of the liquid sprayed from the spray collecting part 30 to the mass of each cylinder 61 measured in the movable mass measurement part 70.

As described above, when the apparatus for measuring the spray mass flux to evaluate the droplet dispersion of the spray device according to one embodiment of the present invention is applied, the masses of the cylinders receiving sprayed liquid are automatically measured, so that spray mass flux distribution according to the sprayed liquid region is automatically calculated, and the droplet dispersion can be easily evaluated.

Figure 4:
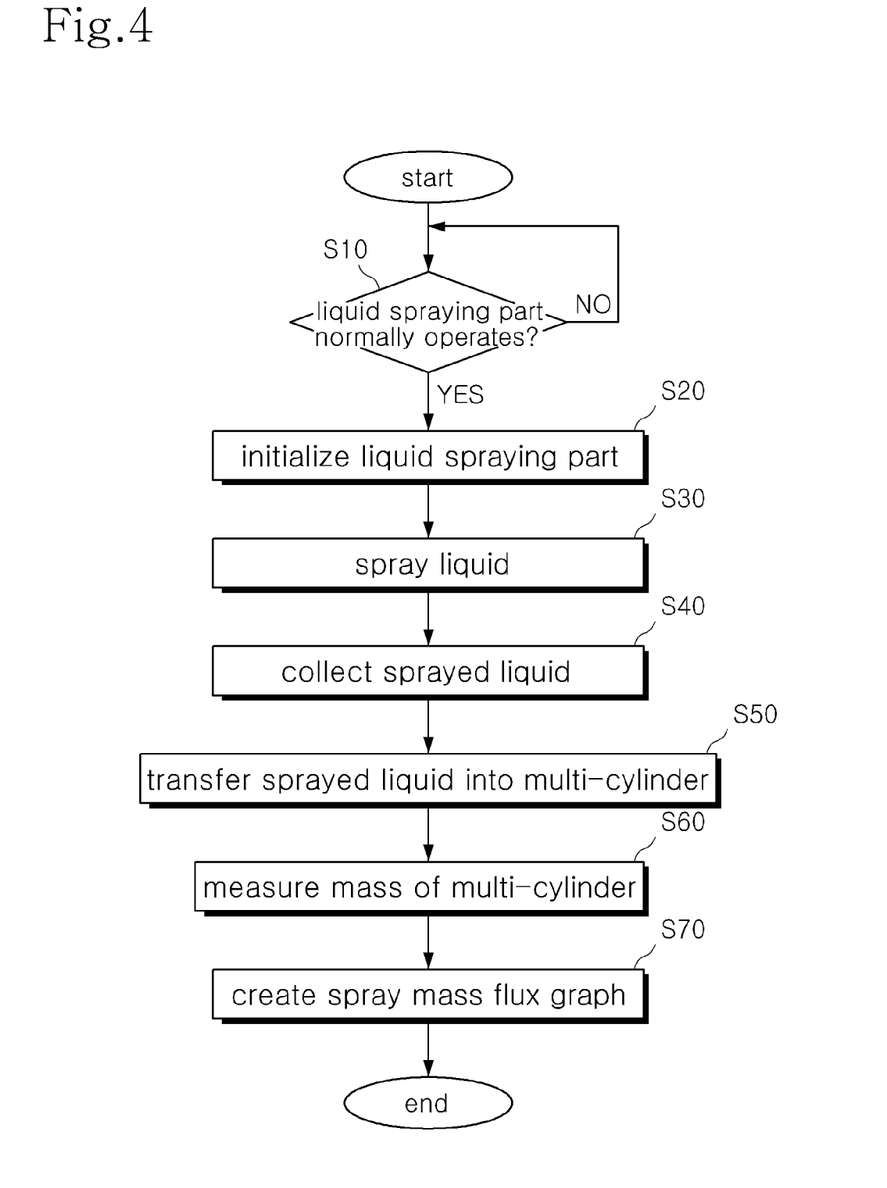
FIG. 4 is a flowchart showing a method for measuring the spray mass flux to evaluate the droplet dispersion of the spray device according to the present invention.

FIG. 4 is a flowchart showing a method for measuring the spray mass flux to evaluate the droplet dispersion of a spray device according to the present invention. First, after closing the spray blocking layer 20, the pressure of spraying liquid in the liquid spraying part 10 is measured to determine if the liquid spraying state of the liquid spraying part 10 is a normal state (step S10).

Next, if the liquid spraying state of the liquid spraying part 10 is determined as a normal sate in step S10, the liquid spraying part 10 is initialized (step S20).

Figure 5:
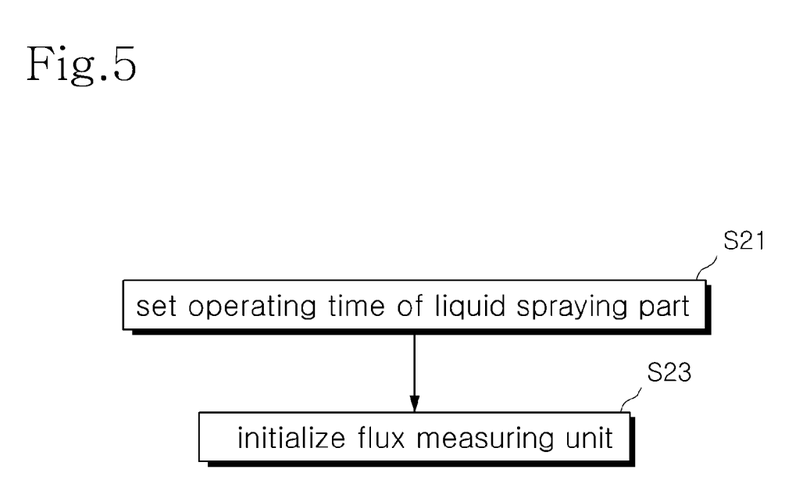
FIG. 5 is a detailed flowchart showing step S20 in the method for measuring the spray mass flux to evaluate the droplet dispersion of the spray device according to the present invention.

FIG. 5 is a detailed flowchart showing step S20 according to the present invention. The operating time of the liquid spraying part 10 is set (step S21), and a flux measuring unit is initialized (step S23).

Through step S20, in a liquid spraying initial stage, liquid can be prevented from being introduced into the spray collecting part 30 according to the imperfect spray operation of the liquid spraying part 10.

Subsequently, the liquid is sprayed through the liquid spraying part 10 (step S30).

In step S30, the liquid includes fuels, paints, and coating agents. In addition, step S30 includes a step of measuring the total mass of sprayed liquid by using the flux measuring unit constituting the liquid spraying part 10.

Thereafter, the sprayed liquid is collected in the spray collecting part 30 (step S40).

Figure 6:
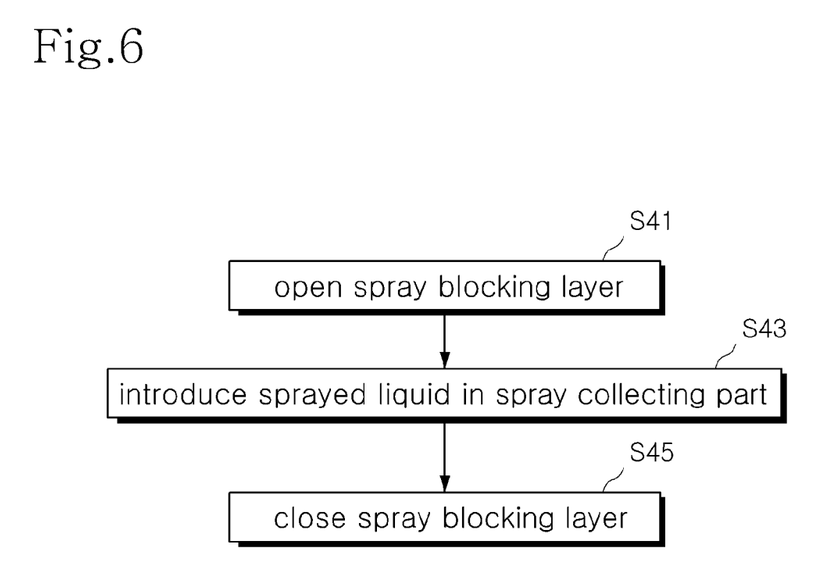
FIG. 6 is a detailed flowchart showing step S40 in the method for measuring the spray mass flux to evaluate the droplet dispersion of the spray device according to the present invention.

FIG. 6 is a detailed flowchart showing step S40 according to the present invention. The spray blocking layer 20 is open (step S41).

Thereafter, the liquid sprayed from the liquid spraying part 10 is introduced into the spray collecting part 30 (step S43), and if the operation of the liquid spraying part 10 is stopped, the spray blocking layer 20 is closed (step S45).

Subsequently, the liquid collected in the spray collecting part 30 is transferred to the multi-cylinder part 60 through the transfer tube 50 (step S50).

Next, the mass of each cylinder 64 of the multi-cylinder part 60 is measured by using the movable mass measurement part 70 (step S60).

Figure 7:
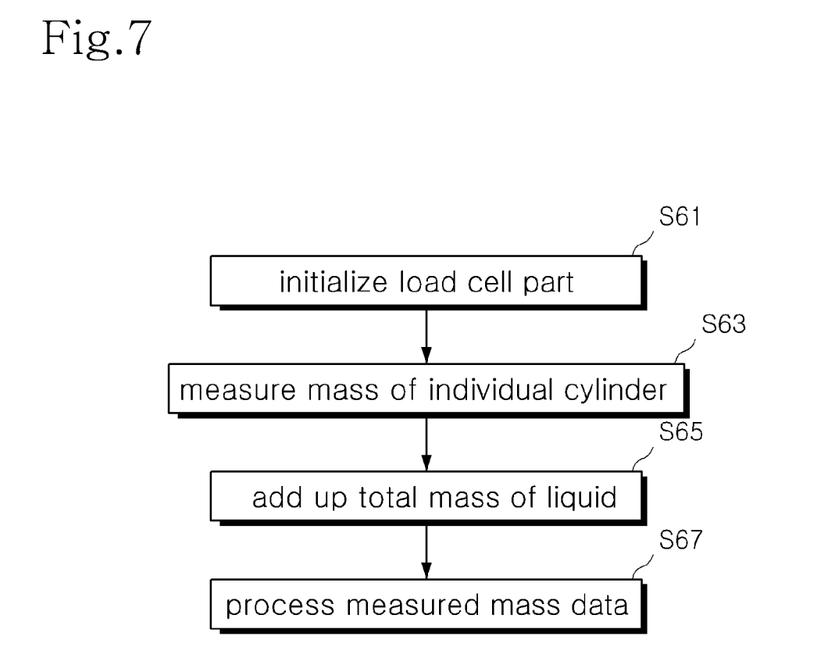
FIG. 7 is a detailed flowchart showing step S60 in the method for measuring the spray mass flux to evaluate the droplet dispersion of the spray device according to the present invention.

FIG. 7 is a detailed flowchart showing step S60 according to the present invention. The movable mass measurement part 70 is initialized (step S61), and the mass of the individual cylinder 61 is measured (step S63). Then, the total mass of the sprayed liquid is obtained (step S65). The measured mass data are processed (step S67).

Subsequently, the 3-D distribution graph of the mass flux of the sprayed liquid is calculated by using the mass flux calculating part (step S70).

According to the present invention, the distribution graph of the mass flux of step S70 is a 3-D mass flux graph obtained by calculating the ratio of the mass of each cylinder 61 to the total mass of the sprayed liquid with respect to the coordinates of the spray collecting part 30.

According to the embodiment of the present invention, the 3-D mass flux graph is calculated by using a Tecplot program after transforming data detected through the load cell part 71 to a data file.

As described above, according to the method for measuring spray mass flux to evaluate the droplet dispersion of the spray device of the present invention, sprayed fuel is collected and transferred to the multi-cylinder, so that 3-D mass flux distribution can be automatically calculated.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

[Industrial Applicability]

As described above, according to the apparatus for measuring the spray mass flux to evaluate the droplet dispersion of a spray device of the present invention, spray mass flux distribution according to liquid spraying regions can be automatically calculated and the droplet dispersion can be easily evaluated by automatically measuring the masses of a plurality of cylinders receiving sprayed liquid.

In addition, liquid which is not introduced into a plurality of lattice cells or a plurality of tubes can be prevented from flowing out by providing a flux loss preventing plate.

In addition, liquid can be prevented from being unstably collected in a liquid spraying initial stage by additionally providing a spray blocking layer.

In addition, a plurality of cylinders constituting a multi-cylinder part can be regularly arranged and the arranged cylinders can be fixed.

In addition, a movable mass measurement part is provided and a load cell part of the movable mass measurement part is movable left, right, forward, or backward, so that the mass of each cylinder can be measured.

In addition, as the ratio of the total mass of the sprayed liquid to the mass of each cylinder is calculated, 3-D mass flux distribution can be exactly calculated.

In addition, the total mass of the sprayed liquid can be calculated by providing a flux measuring unit.

According to the method for measuring the spray mass flux to evaluate the droplet dispersion of the spray device of the present invention, 3-D mass flux distribution according to masses of cylinders can be automatically calculated after collecting sprayed fuel and transferring the sprayed fuel into a multi-cylinder.

In addition, the spraying operation state of the liquid spraying part can be determined as a normal state before liquid is sprayed.

In addition, if the spraying operation state of the liquid spraying part is determined as the normal state, a spray blocking layer can be open to prevent abnormally sprayed liquid from being collected. In addition, the lost liquid flux of the spray collecting part can be measured.

Further, the mass of each cylinder can be exactly measured by initializing a movable mass measurement part.

The invention claimed is:

1. An apparatus for measuring spray mass flux to evaluate droplet dispersion of a spray device, the apparatus comprising:
   a liquid spraying part including a spray nozzle to spray liquid;
   a spray collecting part collecting the liquid sprayed from the liquid spraying part, the spray collecting part including a plurality of lattice cells or a plurality of tubes arranged in a form of matrix;
   a transfer tube transferring the liquid collected in the spray collecting part;
   a multi-cylinder part including a plurality of cylinders accommodating one end of the transfer tube therein to receive the liquid collected in the spray collecting part;
   a movable mass measurement part measuring a mass of each cylinder of the multi-cylinder part;
   a mass flux calculating part linked with the spray collecting part and the movable mass measurement part to calculate a distribution graph of mass flux of the sprayed liquid; and a spray blocking layer disposed above the spray collecting part and configured to block the sprayed liquid such that a liquid spray state of the liquid spraying part can be determined by measuring pressure of spraying liquid in the liquid spraying part after closing the spray blocking layer, before spraying the liquid by using the liquid spraying part.

2. The apparatus of claim 1, wherein the spray collecting part includes a flux loss preventing plate to prevent liquid, which is not introduced into the lattice cells or the tubes, from flowing out.

3. The apparatus of claim 1, wherein the multi-cylinder part includes the cylinders arranged in a form of a matrix while being spaced apart from each other by a predetermined distance, and includes a cylinder holder to fix an outer portion of each cylinder.

4. The apparatus of claim 3, wherein the movable mass measurement part comprises:
 a load cell part to measure the mass of each cylinder; and
 a servo transfer module connected to a lower portion of the load cell part to transfer the load cell part in a row direction or a column direction so that the load cell part moves to a lower point of the cylinder to be measured.

5. The apparatus of claim 1, wherein the mass flux calculating part calculates 3-D mass flux distribution according to a liquid spray region by using a liquid mass ratio of a total mass of the liquid sprayed from the spray collecting part to the mass of each cylinder measured in the movable mass measurement part.

6. The apparatus of claim 1, wherein the liquid spraying part includes a flux measuring unit to measure a total mass of the sprayed liquid.

7. A method for measuring spray mass flux to evaluate droplet dispersion of a spray device, the method comprising:
 spraying liquid by using a liquid spraying part including a plurality of lattice cells or a plurality of tubes arranged in a form of matrix;
 collecting the sprayed liquid by using a spray collecting part;
 measuring a total flux of the liquid sprayed in the spray collecting part by using a flux measuring unit;
 moving the liquid, which is collected in the spray collecting part, to a multi-cylinder part by using a transfer tube;
 measuring masses of cylinders of the multi-cylinder part by using a movable mass measurement part;
 calculating a 3-D mass flux distribution graph of the sprayed liquid by using a mass flux calculating part; and
 determining a liquid spray state of the liquid spraying part by measuring pressure of spraying liquid in the liquid spraying part after closing a spray blocking layer, before spraying the liquid by using the liquid spraying part.

8. The method of claim 7, further comprising opening the spray blocking layer if the liquid spray state of the liquid spraying part is determined as a normal state.

9. The method of claim 8, further comprising initializing the movable mass measurement part before measuring the masses of the cylinders in the multi-cylinder part.

* * * * *